United States Patent [19]

Hwang et al.

[11] Patent Number: 5,116,367
[45] Date of Patent: May 26, 1992

[54] PROSTHETIC HEART VALVE

[75] Inventors: Ned H. C. Hwang, 2155 Lochlevin Dr., Memphis, Tenn. 38119; Jack C. Bokros, Austin, Tex.

[73] Assignees: Ned H. C. Hwang, Memphis, Tenn.; Onx, Inc., Austin, Tex.

[21] Appl. No.: 419,288

[22] Filed: Oct. 10, 1989

Related U.S. Application Data

[63] Continuation-in-part of Ser. No. 392,745, Aug. 11, 1989.

[51] Int. Cl.⁵ .................................................. A61F 2/24
[52] U.S. Cl. ............................................................. 623/2
[58] Field of Search ................................................. 623/2

[56] References Cited

U.S. PATENT DOCUMENTS

| | | | |
|---|---|---|---|
| 4,011,601 | 3/1977 | Clune et al. | 623/2 |
| 4,078,268 | 3/1978 | Possis | 623/2 |
| 4,159,543 | 7/1979 | Carpentier | 623/2 |
| 4,373,216 | 2/1983 | Klawitter | 623/2 |
| 4,425,670 | 1/1984 | Figuera | 623/2 |
| 4,484,365 | 11/1984 | Murguet et al. | 623/2 |
| 4,535,484 | 8/1985 | Marconi | 623/2 |
| 4,872,875 | 10/1989 | Hwang | 623/2 |
| 4,892,540 | 1/1990 | Vallana | 623/2 |

Primary Examiner—Randy C. Shay
Attorney, Agent, or Firm—Fitch, Even, Tabin & Flannery

[57] ABSTRACT

A bi-leaflet heart valve having an improved hinge arrangement that, in combination with the disclosed curved surfaces of the leaflets, allows the valve to respond more quickly to flow reversal and minimizes fluttering of the leaflets in the open position. The leaflets are slidably and pivotally mounted in a heart valve body for movement between closed and open positions. The leaflets have notches which matingly engage complementary surfaces on pivot projections extending inward from the valve body sidewall. The shape and relationship of these complementary surfaces and the two-dimensional curvature of the leaflets provides for improved operating characteristics.

15 Claims, 4 Drawing Sheets

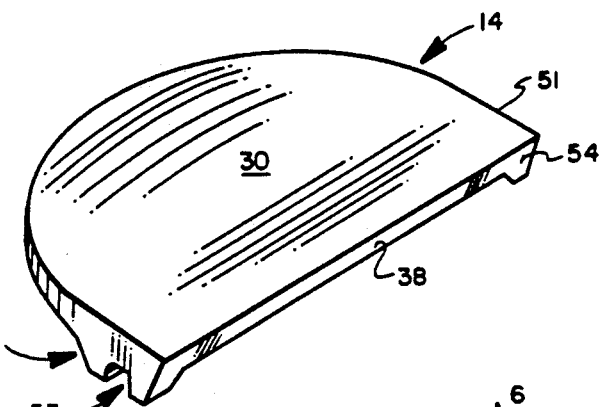
FIG. 4
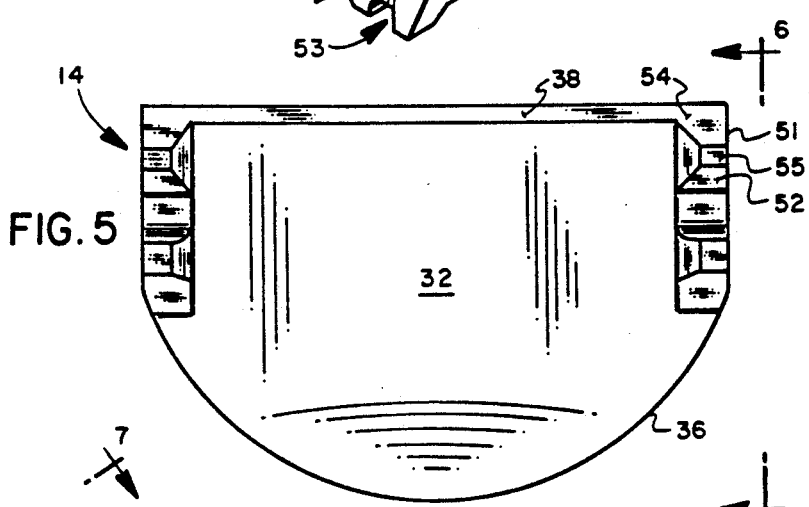
FIG. 5
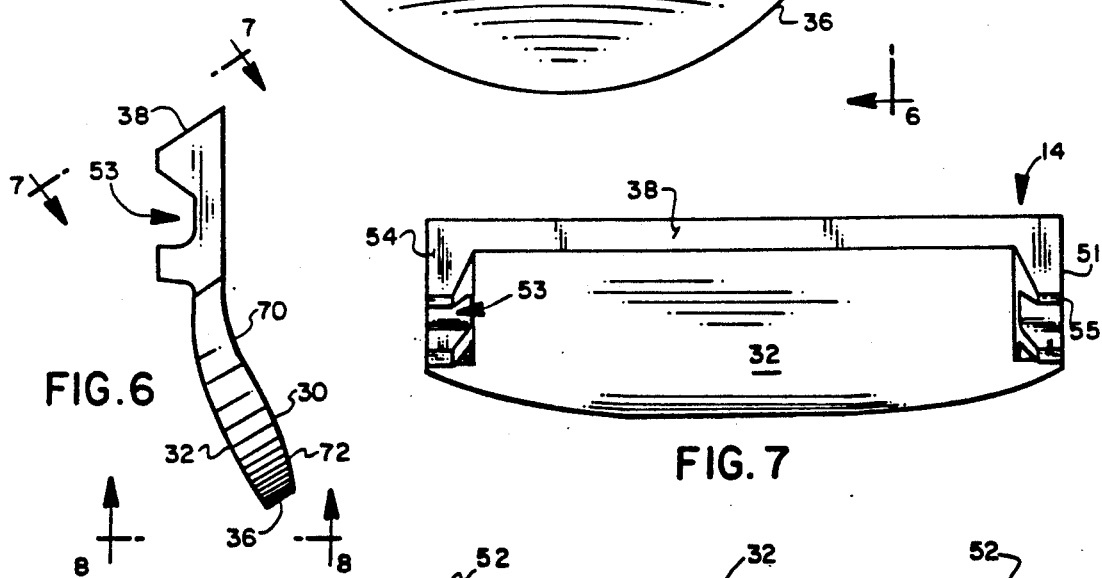
FIG. 6
FIG. 7
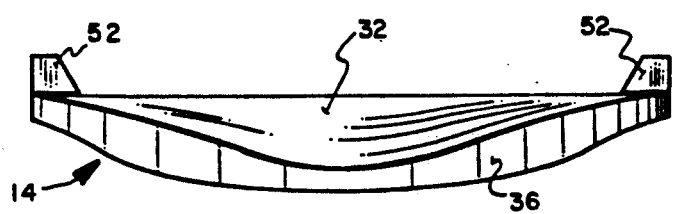
FIG. 8

PROSTHETIC HEART VALVE

This application is a continuation-in-part of our co-pending U.S. patent application Ser. No. 392,745, filed Aug. 11, 1989, allowed.

BACKGROUND OF THE INVENTION

The present invention pertains to heart valve prostheses and in particular, to prosthetic heart valves using pivotable valve members, including bi-leaflet valves.

DESCRIPTION OF THE PRIOR ART

Various types of heart valve prostheses have been developed which operate hemodynamically as a result of the pumping action of the heart. Among the types of heart valves which have been developed are valves having single occluders which pivot along an eccentric axis to open and close the heart valves, such as that described in U.S. Pat. Nos. 4,011,601, 4,423,525 and 4,425,670, and bi-leaflet heart valves, such as those described in U.S. Pat. Nos. 4,484,365 and 4,535,484. The above-mentioned patents illustrate various arrangements for pivotally connecting the valve members or occluders to a valve body and disclose occluders of a variety of shapes. However, most of these designs have never become commercial because of some shortcoming, and the need continues for improved prosthetic heart valves for permanent implantation into the human heart.

In its open position, a prosthetic valve should provide a passageway which is large and which has good flow characteristics so that blood flows freely therethrough without adverse boundary layer separation and with a minimum of drag. The heart valve should be rapidly responsive to blood flow to quickly open during the pumping stroke of the heart and to close quickly when the heart relaxes to prevent substantial regurgitation of the blood. The opening and closing of the valve should be sufficiently soft so that the patient is not disturbed by the sounds produced. The heart valve must, of course, be biocompatible and thrombo-resistant, and in this regard, it is important that all surfaces be well washed by blood to prevent stagnation which might lead to eventual clotting. Furthermore, the action of the valve should be such that it does not cause hemolysis (breaking of blood cells), and of course, the heart valve should be constructed to withstand countless openings and closings.

SUMMARY OF THE INVENTION

The present invention provides heart valves having the aforementioned desirable characteristics wherein the valve occluders, or leaflets, are designed to eliminate boundary layer separation adjacent their surfaces in the open position and thereby minimize drag, resulting in excellent blood flow characteristics therethrough.

These and other objects of the present invention, which will become apparent from studying the appended description and accompanying drawings, are provided in a prosthetic heart valve for allowing blood flow therethrough in a downstream direction. The valve comprises a generally annular valve body having an interior sidewall which defines a central passageway therethrough for the passage of blood in a downstream direction and occluder means having an upstream surface and a downstream surface which is mounted in the valve body to alternately permit the flow of blood therethrough in a downstream direction and block the flow in the reverse direction. The valve body and occluder means have a mounting arrangement by which said occluder means is mounted to generally pivot between an open position and a closed position where blood flow is blocked, which mounting arrangement includes a pair of projections extending inward from the sidewall and a pair of notches in the occluder means for receiving the projections.

Each of the projections may be formed with upstream and downstream flat surfaces oriented at a predetermined angle to each other, and each of the notches may have complementary surfaces.

In another aspect, each of the projections may be formed with at least one flat surface, with each notch having at least one flat surface and a curved surface extending from the downstream edge of the flat surface. In this instance the flat surfaces are positioned so that, when the occluder means is in the open position, the flat surface on each projection is in surface-to-surface contact with the flat surface of each notch so that, upon reversal of the flow of blood through the valve body, the occluder means is immediately displaced slightly upstream causing the curved notch surface to engage the downstream edge of the flat surface of the projection which results in the occluder means immediately beginning to pivot toward its closed position as such upstream displacement begins.

BRIEF DESCRIPTION OF THE DRAWINGS

In the drawings, wherein like elements are referenced alike,

FIG. 4 is a perspective view of a leaflet from the valve shown in FIG. 1.

FIG. 5 is an enlarged elevational view of the leaflet shown in FIG. 4 showing the downstream or backflow surface;

FIG. 6 is a side, elevational view of the leaflet of FIG. 4, looking along line 6—6 of FIG. 5;

FIG. 7 is an elevational view of a leaflet, taken looking along line 7—7 of FIG. 6;

FIG. 8 is an elevational view of a leaflet, taken looking along line 8—8 of FIG. 6;

DETAILED DESCRIPTION OF THE PREFERRED EMBODIMENTS

FIGS. 1—13 show a preferred embodiment of a heart valve prosthesis constructed according to principles of the present invention. The heart valve, generally designated 10, is of a bi-leaflet construction, but it will be readily apparent to one ordinarily skilled in the art that the principles of the present invention can be applied to a prosthetic heart valve having single occluder or single leaf construction.

Both embodiments attain numerous advantages as will be described herein. For example, such heart valves provide an improved flow when the valve is in a fully open position and eliminate boundary layer separation at major surfaces of the leaflets, thus minimizing drag on blood flowing therethrough, while providing excellent wash characteristics so as to prevent stagnation which might lead to eventual clotting. In addition, such embodiments of the heart valve provide a rapid response upon opening and closing, with a relatively small impact when the leaflets contact the valve body, without hemolysis or like injury to blood cells flowing through the valve.

Figure 1:
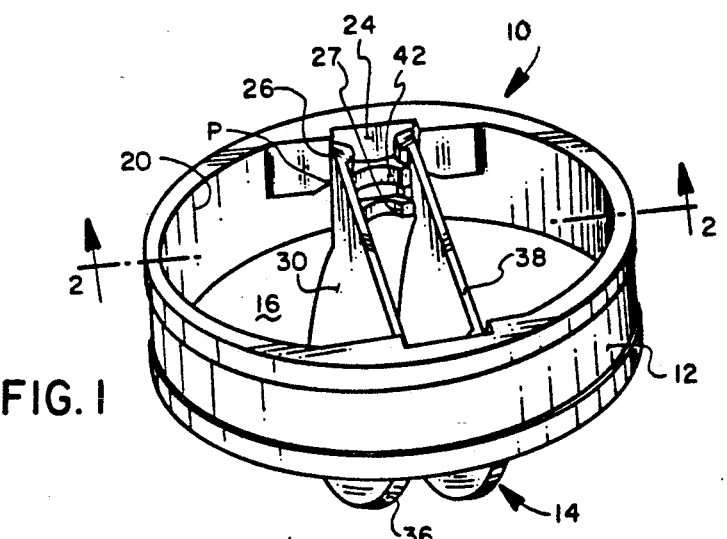
FIG. 1 is a perspective view of a bi-leaflet heart valve embodying various features of the present invention, shown in its open position.
Figure 2:
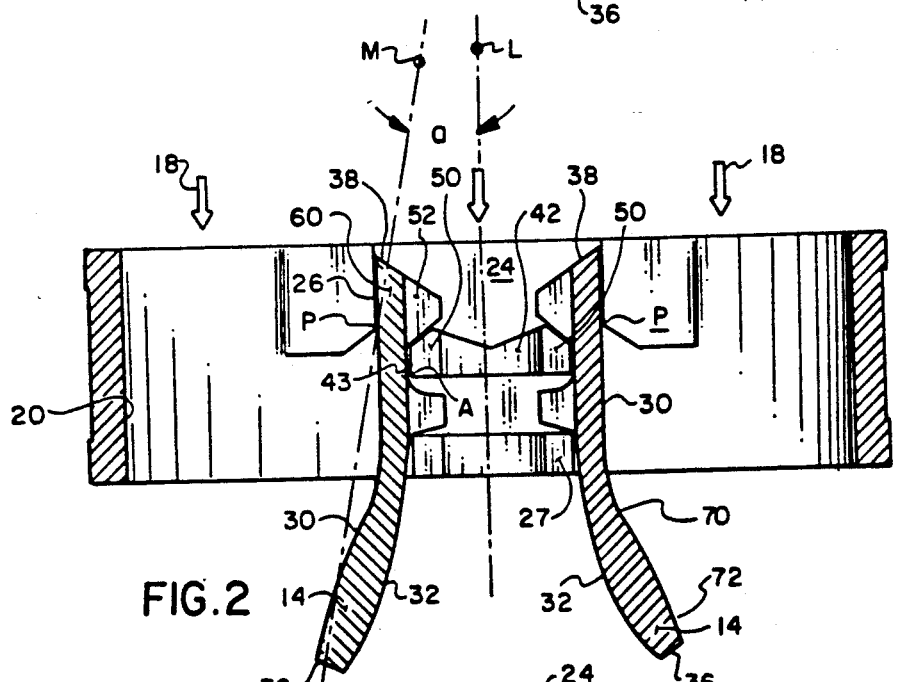
FIG. 2 is an enlarged cross-sectional view of the heart valve taken along the line 2—2 of FIG. 1, showing the valve in its open position.

Referring initially to FIGS. 1-13, heart valve 10 includes a generally annular valve body 12 and carries a pair of pivoting valve occluders or leaflets 14, which open and close to control the normal flow of blood in the downstream direction of arrows 18 (see FIG. 2). Blood flows through passageway 16 which is defined by a generally cylindrical interior surface or sidewall 20 of body 12. Sidewall 20 is interrupted by a pair of diametrically opposed flat wall sections 24 which are perpendicular to the pivot axes of the leaflets. Flanking these flat wall sections are a pair of abutments 26 which act in addition to ledge 27 to stop the rotation of the leaflets when the leaflets are in a fully open position, such as that illustrated in FIG. 1 and 2.

Figure 3:
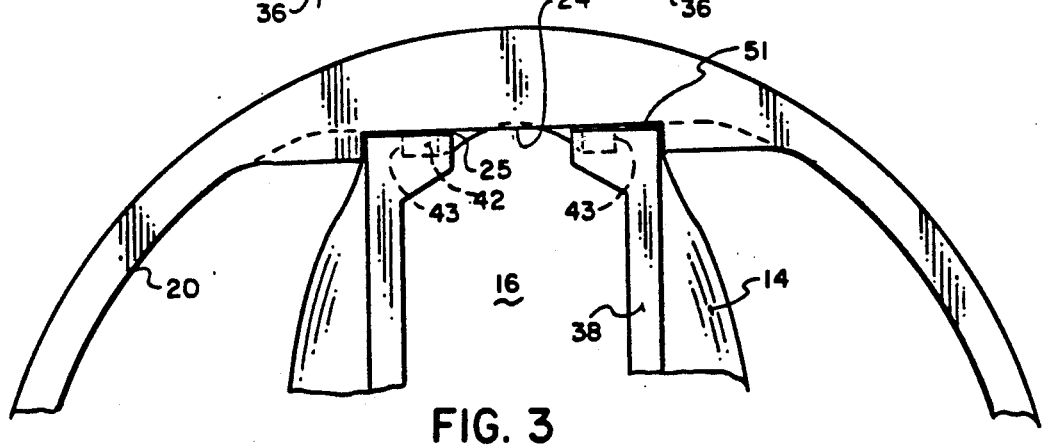
FIG. 3 is a plan view of the bi-leaflet heart valve shown in FIG. 1, showing the valve in an open position.

As best seen in FIGS. 1 through 3, pairs of diametrically opposed pivot projections 42 extend generally perpendicularly from &he flat wall sections 24. Each of the two lateral surfaces 43 of the pivot projections 42 contains three flat seating surfaces 44a, 44b and 44c each oriented between about 110° and about 130°, and preferably approximately 125°, from the flat seating surface adjacent to it. In the preferred embodiment, one of the three flat seating surfaces 44a is oriented generally parallel to &he axis of blood flow, with the other two surfaces 44b and 44c lying on the upstream side 45 of the pivot projections 42. (See FIGS. 12 and 13) The center sections 47 of the pivot projections 42 are concave with respect to the central axis L (FIG. 2) of the valve body 12 so as to minimize the transverse area exposed to, and impeding, the flow of blood through the passageway 16. The opposite end portions 50 of the pivot projections 42 include the lateral surfaces 43 and have flat interior surfaces which are generally parallel to the flat wall section 24 of the valve body. Thus, the three seating surfaces 44a, 44b, and 44c of each upstream end of the pivot projections 42 are perpendicular to, and extend between, the parallel surfaces of the flat wall section 24 of the valve body and the flat portion 50 of the pivot projection 42. Thus, the seating surfaces 44a, 44b and 44c are parallel to the pivot axes of the leaflets. As discussed below, these pivot projections 42 are matingly engaged with notches 53 formed in the leaflets 14.

Referring now to FIG. 2, leaflets 14 have an upstream or inflow surface 30 and an opposed downstream or backflow surface 32. With the cross-sectional view of FIG. 2, which is taken along the central, major axis of the leaflets, it is apparent that the cross-sectional thickness of the leaflets varies considerably from one end of the leaflet to the other. This is to minimize impedance of the heart valve to blood flowing therethrough by employing a three-dimensional composite curvature formed by a cooperation of the leaflet inflow and backflow major surfaces. As described in U.S. patent application Ser. No. 296,428, now U.S. Pat. No. 4,872,875 the disclosure of which is incorporated herein by reference, the novel three-dimensional composite curvature of the leaflets provides maximum flow area at the valvular orifice and reduces boundary layer separation adjacent the major leaflet surfaces when the leaflets are in the open position, so as to minimize drag imparted to blood flowing through the heart valve, resulting in excellent blood flow characteristics. The unique curvature of the leaflets also provides for a more rapid response of the leaflets to reversals in the direction of blood flow than is attained with flat leaflets. The increased responsiveness of the leaflets attributable to their curved surface acts in conjunction with the increased responsiveness attained by the hinge mechanism herein described t provide a heart valve having, in one of its aspects, heretofore unattainable rapidity of initial opening and closing in response to reversals of blood flow through the valve.

The inflow surfaces 30 of the leaflets have a concave region 70 of two-dimensional curvature, thus resembling a curved sheet. As used herein, a two-dimensional curved surface is one which comprises a plurality of straight lines which define a curved surface, each of which lines is parallel to a straight line axis. Thus, planes including the axis will cut the two-dimensional surface along straight lines, and planes perpendicular to the axis will cut the two-dimensional surface along curved lines. According to other principles of the present invention, the leaflet inflow surfaces 30 also include a convex region 72 of generally two-dimensional curvature, downstream of the concave region 70. Convex region 72 may have a curvature resembling a paraboloid, an ellipsoid or some other smoothly curved cross section shape. In the preferred embodiment, the various portions of the major leaflet surfaces are blended so as to be continuously smooth, without interruptions or discontinuities.

According to another aspect of U.S. patent application Ser. No. 296,428, the backflow surfaces 32 of the leaflets 14 preferably have convex surface regions, at least for those portions of the outflow surfaces 32 which oppose the inflow concave regions 70 and the inflow convex regions 72. The leaflets have a maximum thickness where the convex surfaces 32, 72 oppose one another, adjacent the trailing end of an opened valve. It will be noted that the opposed convex surfaces do not meet at a line, but rather are truncated by the major arcuate edge 36, which preferably has a substantial thickness to provide a reliable, low noise, reduced leakage mating with the valve body upon valve closing. The leaflets 14 are characterized, in one aspect, by having concave and convex surfaces 70, 72 and 32 of two-dimensional curvature, which surfaces are formed of curved lines which are generally parallel to the leaflet pivot axes. Preferably, these curved surface portions are all downstream of the pivot axis, although such is not always required.

The leaflets 14 have a major arcuate surface or outer edge 36 which is located at the trailing portions of a fully opened leaflet. A minor surface or inner edge 38 is located at the opposite, leading end of the leaflet (again, assuming a leaflet in an open position). The curved major surface 36 is preferably arcuate in configuration. The minor surface 38 is preferably of a straight-line configuration so as to present a relatively flat mating surface to the opposing leaflet. This minor surface 38 is tapered inward toward the backflow side 32 of the leaflet 14 at an obtuse angle such that the two minor surfaces 38 of the leaflets 14 abut along substantially their entire length when the valve is in the closed position.

Referring to FIGS. 4 and 5, leaflets 14 include a pair of opposed, lateral surfaces 51 which are interposed between the major arcuate surface 36 and the minor straight-line mating surface 38. These lateral surfaces 51 of the leaflets are preferably flat, and the leaflets are proportioned so as to provide a minimal clearance 25 with the flat wall sections 24 of the valve body 12 (See FIG. 3). This is to enable the leaflets 14 to pivot adjacent the flat wall sections 24 about pivot axes which are perpendicular thereto.

Figure 9:
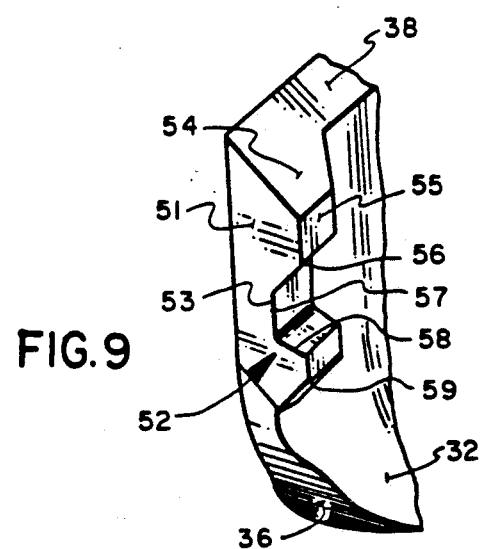
FIG. 9 is a perspective, fragmentary, view of the leaflet shown in FIG. 4, particularly illustrating the notch in the extension of the leaflet.

Referring to FIG. 9, extending from the backflow surface 32 at the lateral surfaces 51 of both leaflets 14 are extensions 52. These extensions 52 are generally perpendicular to the backflow surface 32, and have an upstream side 54 and downstream side 59. The upstream side 54 of the extension 52 is tapered, or truncated, toward the backflow side 32 of the leaflet 14 so as to form a continuous, smooth surface with the tapered minor surface 38. The opposed minor mating surfaces 38 and the extensions 52 are truncated so as to give the surfaces a substantial thickness which, as will now be seen, gives several advantages on valve closing. For example, the increased surface area of the mating surfaces 38 distributes forces over a greater area upon contact between mating surfaces, thus reducing stress wear on the leaflets. Also, with the valve in a fully closed position, the increased surface area provides an elongated path between the leaflet mating surfaces which deters leakage.

Figure 12:
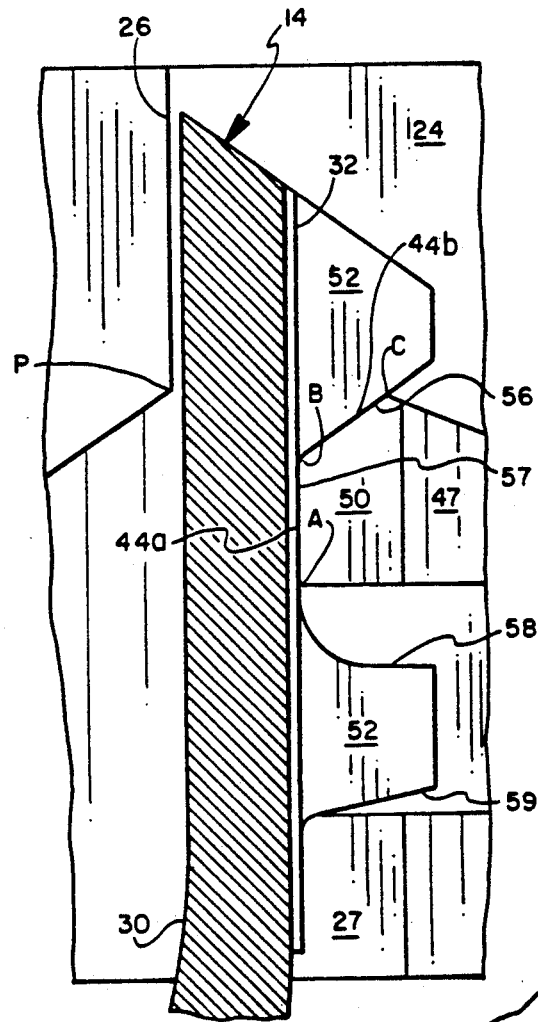
FIG. 12 is an enlarged, fragmentary, cross-sectional view showing the mating engagement between the pivot projection and the leaflet notch with the valve in its open position.
Figure 13:
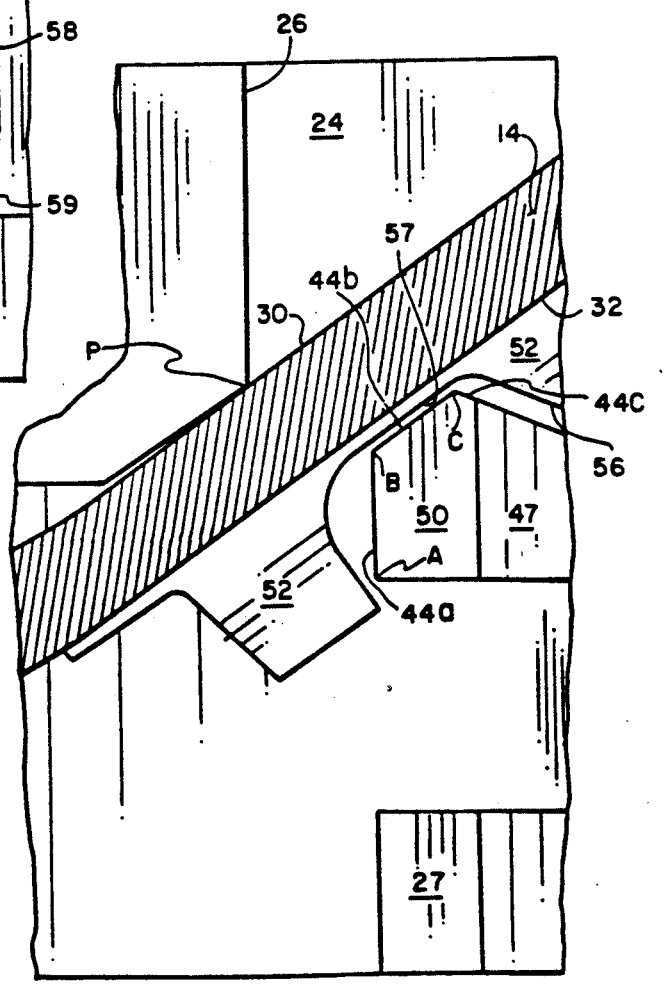
FIG. 13 is an enlarged, fragmentary, cross-sectional view showing the mating engagement between the pivot projection and the leaflet notch with the valve in its closed position.

Notches 53 are formed in each extension 52 extending inward from the free end surface 55 of the extension. As best seen in FIGS. 9, 12 and 13, the notches 53 have two flat or straight surfaces 56 and 57 oriented so as to mate with the surfaces 44a and 44b, e.g., at an angle of about 125° with respect to each other, and a third, curved surface 58. In the preferred embodiment, a first straight surface 57 is substantially parallel and preferably coplanar with the inflow surface 32 of the leaflet, with the second straight surface 56 adjacent and on the upstream side thereof (with the leaflet in the open position). Furthermore, the curved surface 58 is adjacent, and on the downstream side of, the first straight portion 57, and it extends smoothly therefrom, being preferably tangential thereto. The downstream side 59 of the extensions 52 are tapered toward the leaflet 14 to minimize impedance to blood flow through the valve passageway 16.

Referring to FIG. 2, it should be noted that extensions 52 also serve to provide additional structural support to the upstream or leading end portions 60 of the leaflets 14. As described in U.S. patent application Ser. No. 296,428, the upstream or leading end portions 60 of the leaflets 14, i.e., those portions adjacent the minor mating edge 38 which is located at the leading end of a leaflet in an open position, have a significantly reduced thickness, as is apparent from the cross-sectional views of FIGS. 2 and 10. Extensions 52 are preferably formed integral with the leaflets 14 so that there is essentially an increased thickness of the leaflets 14 at the location of the extensions 52 which strengthens the leaflet at the lateral edges 50.

The leaflets 14 are installed in the valve body 12 by squeezing the body at diametrically opposed locations, i.e. those where the valve body is cut by the reference line 2—2 in FIG. 1. This causes the diametrically opposed flat wall sections 24 to further separate, thus allowing the leaflets 14 to be slid into the passageway 16 of the valve body. The extensions 52 of the leaflets are secured between the ends of the pivot projection 42 and the portion of the valve body which serves as an abutment 26. The flat end portions 50 of the pivot projections 42 are received in the notches 53. The squeezing force is then removed allowing the flat wall sections 24 to return to their original spacing, with a minimal clearance between the flat wall sections 24 of the valve body 12 and the lateral surfaces 51 of the leaflets as discussed above. The notches 53 in the leaflet extensions 52 matingly engage with the pivot projections 42 to allow the leaflets to slidably and pivotally rotate between open and closed positions. This is discussed further below in relation to the operation of the valve.

Referring to FIG. 3, the lateral surfaces 51 and extensions 52 of the leaflets 14 are preferably dimensioned to provide a small clearance 25 with the corresponding adjacent flat wall sections 24 of valve body 12.

As will now be appreciated by those skilled in the art, the leaflets and heart valve body have relatively simple configurations which are easy to machine and which also provide an improved economical fabrication, in that tolerances of the heart valve components are easily maintained.

The leaflets are slidably and pivotally mounted for rotation between closed and open positions, and it is generally preferred that the opening, and particularly the closing, motions of the leaflets be made as rapid as possible. However, the end points of the termination of movement of the leaflets should be well defined to reduce noise and leaflet wear. For example, the leaflets should not bounce back when contacting seating surfaces defining the end points of their travel, nor should the major surfaces 36 extend beyond the valve body 12 when in a closed position. As will now be seen, such advantages are attained with the present invention.

FIG. 1 shows the inflow surfaces 30 of leaflets 14 lying adjacent the relatively flat abutments 26 which, along with ledges 27, define the extent of opening of the leaflets, thus fixing one end of their travel. Ledges 27 extend inwardly from the flat wall sections 24 and are located downstream of the pivot projections. Similar to the pivot projections, the center of the ledges 27 are preferably concave with respect to the central axis L of the valve body 12 so as to minimize the transverse area exposed to, and impeding, the flow of blood through the passageway 16. Employing ledges 27 in addition to abutments 26 to stop rotation of the leaflets 14 results in less wear on both the ledges and abutments as each, individually, encounters less force upon impact. The closing end of the leaflet travel is defined by the abutting of the minor, mating surfaces 38 of the leaflets, and/or the contacting of the major, arcuate, surfaces 36 with the interior surface or sidewall 20 of the valve body 12 which has formed therein a seating region. There is likely also contact along edge P (FIG. 13).

With reference to FIG. 2, abutments 26 and ledges 27, in combination with a pivot projection 42, and more particularly the flat seating surfaces 44a and 44b, define the fully open position of leaflets 14. In the preferred embodiment, the mating flat surfaces 38 do not extend beyond the valve body when the leaflets are in their open position (see FIGS. 2 and 12). It is generally desirable to orient the fully open leaflets for minimum obstruction of the downstream flow through the valve body passageway 16. As can be seen in FIG. 2, the flat upstream and downstream portions 60 of the leaflets 14 are oriented essentially parallel to the direction of blood flow, generally indicated by arrows 18.

The leaflets 14 undergo a controlled angular displacement between their fully closed and fully open positions. With reference to FIG. 2, the angle of opening (i.e. the angular orientation of the leaflets when in the open position) identified by the reference letter a has a value ranging between about 1° and about 20°. Preferably, the angle of opening of the leaflets has a value ranging between about 5° and about 20°, and most preferably, has an angle ranging between about 7° and about 13°. As used herein, the term "angle of opening" is defined as the angle between a plane which both longitudinally bisects the minor mating surface 38 and also contains the midpoint of the major arcuate surface 36 (see reference character M in FIG. 2) and the centerline of the valve body passageway (see reference character L in FIG. 2).

Figure 10:
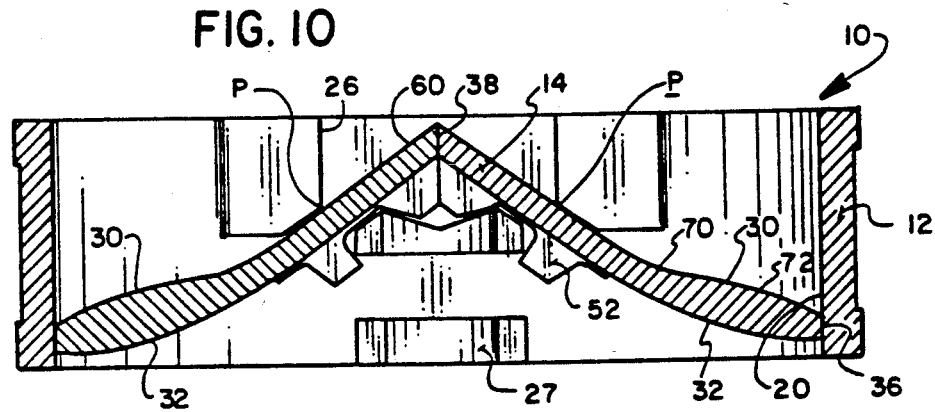
FIG. 10 is a cross-sectional view of the heart valve showing the valve in its closed position.

Referring to FIG. 2, the centerline L of the passageway 16 through the valve body 10 lies midway between the pivot axes of the pivot projections 42 disposed adjacent a given flat wall section 24. In the fully open position illustrated in FIG. 2, the backflow surfaces of the leaflets 32 lie opposed to one another on opposite sides of the centerline L, and the portions of the inflow and backflow surfaces 30 and 32 of the leaflets 14 within the valve body 12 extend generally parallel to the central axis L. In the fully closed position as shown in FIG. 10, the minor, mating surfaces 38 of the leaflets 14 abut one another. No matter which opening angle a is chosen, it is generally preferred that the leaflets 14 are not brought into a generally straight-line relationship when fully closed, in order to avoid a risk of wedging of the leaflets. Instead, the leaflets 14 should have an obtuse angular relation to one another as shown in FIGS. 10 and 11, preferably less than about 150°.

Figure 11:
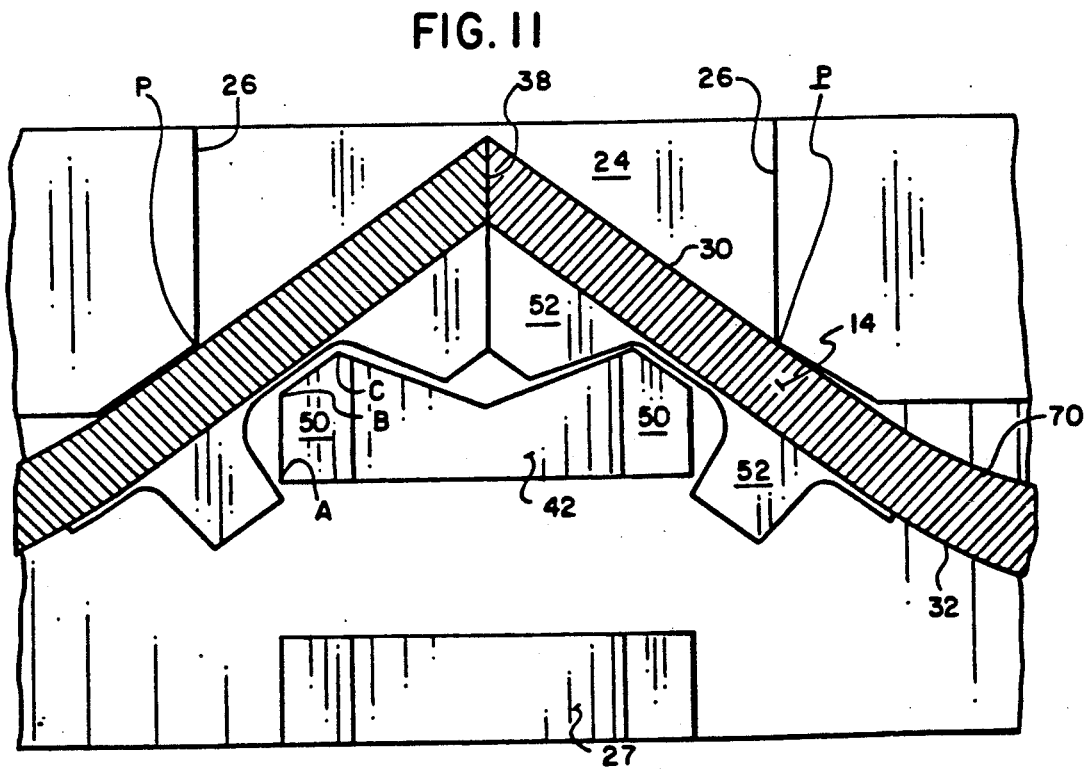
FIG. 11 is an enlarged fragmentary, cross-sectional view showing the mating engagement between the pivot projection and the leaflet notch with the valve in its closed position.

With reference to FIGS. 2 through 13, operation of the heart valve 10 will now be described assuming an initial, fully closed position. In the fully closed position, as shown in FIGS. 10, 11, and 13, the two flat surfaces 56 and 57 of the notch 53 of each of the leaflets lie adjacent to the two upstream flat seating surfaces 44b and 44c of the pivot projection 42, and there is a small clearance between these adjacent surfaces. When the cardiac cycle reverses, blood flows in the direction of the arrows 18 (FIG. 2). During initial valve opening movement, the leaflets are displaced in the downstream direction until the flat surfaces 56 and 57 of the leaflet notches 53 are pressed against the upstream seating surfaces 44b and 44c of the pivot projections 42. Due to the fact that the inflow surfaces 30 of the leaflets have greater surface area on the portions thereof which lie downstream of the pivot projections 42 than on the portions upstream of the pivot projections 42 (FIG. 2), i.e. the notches 53 are located closer to the minor mating surfaces 38 than the major surfaces 36, a moment imbalance is developed between the downstream portions of the inflow surfaces and the upstream portions of the inflow surfaces. This causes the leaflets 14 to begin to pivot about the pivot projections 42 in the direction of valve opening, with their minor mating surfaces 38 being spread apart, and their major surfaces 36 being advanced toward one another. There is no contact of the leaflets with the edge L of abutment 26 during leaflet opening. There is possible contact between the leaflets and the edge P during the period that the leaflets are maintained in the fully open position. Force on the pivot projections 42 decreases as the leaflets 14 open, due to reduced leaflet cross-sectional area interfering with the blood flow. As the leaflets 14 approach a more open position, the points of contact of the notches 53 with the edges B and C of the pivot projections 42 continuously changes. The effect of this shifting of the points of contact is discussed below.

Referring now to FIG. 2, the opening movement of the leaflets is stopped when the inflow surfaces 30 thereof contact the flat abutments 26 and/or the outflow surfaces 32 contact the ledges 27. The abutments 26 are preferably oriented in a direction parallel to the central axis L of the valve body so as to orient the fully open leaflets in a direction which presents minimal interference to the blood flow.

In the fully open position, the two flat surfaces 56 and 57 of the leaflet notches 53 are matingly engaged with the flat seating surface 44a parallel to the flow of blood and the upstream, flat seating surface 44b immediately adjacent to it (see FIG. 12). The two complementary pairs of surfaces in contact with each other provide a stable, non-flattering orientation of the leaflet 14 in the fully open position.

Upon a reversal of the cardiac cycle, blood flow develops in an upstream direction, generally opposite that of the arrows 18 of FIG. 2. Referring initially to FIG. 2, the force of back-flowing blood against the leaflet outflow surface 32 causes the leaflets 14 to begin to pivot in a closing direction, and aided by drag forces on the leaflet surfaces, the leaflets are shifted slightly upstream, i.e. in an upward direction as depicted in FIGS. 2, 12, and 13. Upon this shifting of the leaflet, there is engagement between the edge labeled A on the stationary pivot projection 42 and the curved surface 58 of the leaflet notch 53 (see FIGS. 12 and 13) and contact with the edge P of the lower edge of the abutment 26. This acts to provide an initial, rapid pivoting of the leaflet 14 in a closing direction which, in turn, exposes a greater portion of the outflow surface 32 of the leaflet to the force of the backflowing bloodstream. As greater portions of the leaflet outflow surfaces 32 become more transversely aligned with the blood stream, the rate of closing increases.

The closing movement of the leaflets is stopped upon contact between the minor, mating edge surfaces 38 of the leaflets and/or contact of the major, arcuate edge surfaces 36 with the interior surface or sidewall 20 of the valve body 12 which may have a seating region formed therein. It should be noted that throughout much of the leaflet closing, there is contact between the inflow surface 30 and the edge P on abutment 26. The leaflets come to rest in the fully closed position of FIGS. 10, 11, and 13 with the edge P on abutment 26 in contact with the inflow surface 30, in preparation for reversal of the cardiac cycle and a subsequent opening operation.

In U.S. patent application Ser. No. 392,745, filed Aug. 11, 1989, an additional advantage of the hinge mechanism of the present invention over conventional hinge mechanisms is discussed. At the beginning of leaflet closing, a large closing moment is favored which will make the leaflet respond quickly to flow reversal. However, as the closing movement continues, the instantaneous center (IC) of points on the leaflet varies, due to the charging points of contact between the notches 53 and projections 42, to result in a reduced impact when the leaflet 14 edge surface 36 contacts the valve sidewall, relative to the impact a similar valve member would have rotating on a pivot of circular cross-section. Likewise, during the initial opening movement of the leaflet 14, a large opening moment is favored which will make the leaflet respond quickly to flow reversal. As the opening movement continues, IC migrates so as to also result in a reduced impact when the leaflet 14 contacts the abutment 26 or the ledge 27.

As previously mentioned, the shape of the curved-surface leaflets likewise results in the leaflets pivoting rapidly upon initial opening movement, with the rapidity of pivoting decreasing as the leaflets approach their fully open position. Combining the curved-surface leaflets with the above-described hinge mechanism allows this characteristic of the leaflets to act in combination with the same beneficial attribute of the hinge mechanism to provide a heart valve having heretofore unattainable rapidity in its initial opening movement while still being free of undesirable noise and/or bounceback of the leaflets upon contact at final opening. Also, valve closing, in a valve constructed according to principles of the present invention, has been found to be free of noise and bounce-back. Additionally, the seating of the leaflets in a fully closed position has been found to be smooth and reliable, while the seating of the leaflets in the fully open position has been found to be non-fluttering and reliable.

It can be seen from the above that the embodiments of a heart valve 10 constructed according to principles of the present invention obtain numerous advantages, including a heretofore unavailable economical manufacture of the heart valve components. The cooperation of the inflow and outflow surface configurations of the heart valve leaflet provide unprecedented reductions in drag on blood flow through the fully opened heart valve. The surface configurations of the leaflets are not, however, difficult to machine, and preferably consist of combinations of two-dimensional curvatures.

A description of the present forms of the invention having been described by way of example, it is anticipated that variations of the described forms of the apparatus may be made without departing from the invention and the scope of the appended claims.

What is claimed is:

1. A prosthetic heart valve which comprises
  a generally annular valve body having an interior sidewall which defines a central passageway therethrough for the passage of blood in a downstream direction, said interior sidewall being arcuate except for a pair of diametrically opposed flat sidewall sections,
  a pair of occluders each having an upstream surface and a downstream surface, which occluders are mounted in said valve body so as to alternately permit the flow of blood therethrough in a downstream direction and block the flow of blood in a reverse direction,
  said valve body having projections extending radially inward from a central region of each of said flat sidewall sections,
  said occluders each having a pair of notches for receiving said projections so that said occluders pivot each about an eccentric axis, which axis is perpendicular to said flat sidewall sections and is defined by said projections, moving alternately between an open position and a closed position,
  said upstream surface of each of said occluders being formed with a concave region of two-dimensional curvature and with a generally convex region of two-dimensional curvature, said concave surface region being spaced downstream from said pivot axis in said open position and being formed of straight lines which are generally parallel to said pivot axis, said convex region being spaced further downstream from said pivot axis than said concave region,
  each of said projections being formed with two flat surfaces that are parallel to said pivot axis and oriented at a predetermined angle to each other, each of said notches having two flat surface portions oriented at said same predetermined angle to each other, and
  said respective projection flat surfaces and notch surface portions being positioned so that, when each said occluder is in the open position, said pair of flat surfaces on said projections are respectively in surface-to-surface contact with said flat surface portions in said notches.

2. A prosthetic heart valve according to claim 1 wherein each of said notches has a curved surface portion extending from a downstream edge of one of said flat surface portions whereby, when reversal of flow of blood through said valve body causes each said occluder to be immediately displaced slightly upstream, said curved notch surface portion engages an edge of one of said projection flat surfaces, resulting in said occluder immediately beginning to pivot towards its closed position.

3. A prosthetic heart valve according to claim 1 wherein said valve body includes a pair of abutments extending radially inward from each of said interior sidewall flat sections, one of said abutments being spaced from each of said projections and being located so that said upstream surface of each said occluder engages said respective abutment as said occluder pivots from the open to the closed position.

4. A prosthetic heart valve according to claim 3 wherein one of said two flat surfaces of each said projection is oriented substantially parallel to the longitudinal axis of said valve body central passageway, wherein said two flat surfaces of said projections meet along an intermediate straight edge and wherein said occluders engage straight edge regions formed on said abutments which regions are located axially upstream of said projection intermediate straight edges.

5. A prosthetic heart valve according to claim 4 wherein said predetermined angle is between about 110° and about 130°.

6. A prosthetic heart valve according to claim 2 wherein each said occluder is formed with a first generally flat body section and with a second adjacent arcuate body section, said second body section being located downstream of said first section with said occluder in the open position, having formed therein said concave region and said generally convex region, and having a smoothly convex downstream surface, and wherein said flat body section has a pair of enlargements which extend from the downstream surface of said first body section with said notches being formed in said enlargements.

7. A prosthetic heart valve according to claim 6 wherein each of said occluders has an arcuate major edge surface and a generally straight minor mating edge surface, said mating edge surfaces of said pair of occluders abutting each other in said closed position and said major edge surfaces lying adjacent said interior sidewall of said valve body.

8. A prosthetic heart valve according to claim 7 wherein said first generally flat occluder body section of each occluder is aligned substantially parallel to the longitudinal axis of said valve body passageway in the open position and said second arcuate body section is curved so that a plane which longitudinally bisects said mating edge surface and contains the midpoint of said major arcuate edge surface is oriented at an angle of between about 5° and about 20° to said longitudinal axis of said valve body passageway when said occluder is in its open position.

9. A prosthetic heart valve according to claim 6 wherein said valve body includes radially inwardly projecting ledges located at positions spaced downstream from said projections, said occluder downstream surfaces abutting said ledges when said occluders are in the fully open position.

10. A prosthetic heart valve which comprises
a generally annular valve body having an interior sidewall which defines a central passageway therethrough for the passage of blood in a downstream direction, said passageway having a longitudinal axis,
a pair of occluders each having an upstream surface and a downstream surface, said occluders being mounted in said valve body so as to generally pivot about eccentric axes to alternately permit the flow of blood therethrough in a downstream direction in an open position and block the flow of blood in the reverse direction in a closed position.
each of said occluders having a first generally flat body section and a second adjacent arcuate body section, the downstream surface of said second section being convex and curving away from said longitudinal axis of the central passageway, and said second section being downstream from said first section when said occluder is in the open position,
said valve body including a pair of projections extending inward from said sidewall,
said occluders having a pair of notches formed in said first body section thereof for receiving said projections,
each of said projections being formed with at least one flat surface while terminates in a straight edge, each of said notches having at least one flat surface section and a curved surface section, said flat surface section and said curved surface section meeting along a straight line and said curved surface section lying downstream of said flat surface section when said occluder is in the open position, and
each said flat projection surface being positioned so as to be in surface-to-surface contact with said flat surface section in said respective notch when said occluder is in the open position, whereby, when reversal of flow of blood in said valve body and against said convex downstream surface of said occluder second section causes said occluder to be displaced upstream, said curved notch surface sections immediately engage said projection straight edges resulting in each said occluder immediately beginning to pivot towards its closed position as said upstream displacement begins.

11. A prosthetic heart valve according to claim 10 wherein said flat surface of each said projection is oriented substantially parallel to the longitudinal axis of said central passageway.

12. A prosthetic heart valve according to claim 1 wherein said first body section of each said occluder has a pair of lateral enlargements extending from the downstream surface thereof, with said notches being formed in said enlargements.

13. A prosthetic heart valve according to claim 12 wherein said upstream surface of each of said second occluder body sections is formed with a concave region of two-dimensional curvature and with an adjacent generally convex region of two-dimensional curvature, said concave surface region being spaced downstream from the pivot axis of said occluder in the open position and being curved about a straight line which is generally parallel to said pivot axis, and said convex region being downstream from said concave region in the open position.

14. A prosthetic heart valve according to claim 13 wherein each of said two occluders has an arcuate major edge surface and a generally straight minor mating edge surface, said minor mating edge surfaces abutting each other in said closed position and said major edge surfaces lying adjacent said interior sidewall of said valve body.

15. A prosthetic heart valve according to claim 14 wherein said generally flat occluder first body section is aligned substantially parallel to said longitudinal axis of said central passageway in the open position and wherein said second body section is curved so that a plane which longitudinally bisects said minor mating edge surface and contains the downstream midpoint of said major edge surface is oriented at an angle of between about 5° and about 20° to the longitudinal axis of said valve body passageway when said occluder is in its open position.

* * * * *